(12) United States Patent
Grunlan et al.

(10) Patent No.: US 11,707,554 B2
(45) Date of Patent: Jul. 25, 2023

(54) CARTILAGE MIMETIC GELS

(71) Applicant: The Texas A&M University System, College Station, TX (US)

(72) Inventors: Melissa A. Grunlan, College Station, TX (US); Anna Kristen Means, College Station, TX (US)

(73) Assignee: The Texas A&M University System, College Station, TX (US)

( * ) Notice: Subject to any disclaimer, the term of this patent is extended or adjusted under 35 U.S.C. 154(b) by 455 days.

(21) Appl. No.: 16/857,778

(22) Filed: Apr. 24, 2020

(65) Prior Publication Data

US 2020/0338236 A1 Oct. 29, 2020

Related U.S. Application Data

(60) Provisional application No. 62/838,131, filed on Apr. 24, 2019.

(51) Int. Cl.

| | |
|---|---|
| *A61L 27/52* | (2006.01) |
| *A61L 27/26* | (2006.01) |
| *A61L 27/56* | (2006.01) |
| *A61L 27/34* | (2006.01) |
| *C08L 33/26* | (2006.01) |
| *C08J 3/075* | (2006.01) |
| *C08J 7/04* | (2020.01) |

(52) U.S. Cl.
CPC ............... *A61L 27/52* (2013.01); *A61L 27/26* (2013.01); *A61L 27/34* (2013.01); *A61L 27/56* (2013.01); *C08J 3/075* (2013.01); *C08J 7/0427* (2020.01); *C08L 33/26* (2013.01); *A61L 2430/06* (2013.01); *C08J 2333/26* (2013.01); *C08J 2433/26* (2013.01); *C08J 2479/02* (2013.01); *C08L 2203/02* (2013.01); *C08L 2312/00* (2013.01)

(58) Field of Classification Search
CPC ....................................................... A61L 27/52
See application file for complete search history.

(56) References Cited

PUBLICATIONS

Yan et al, Construction of Injectable Double Network Hydrogels for Cell Delivery, Biomacromolecules, 18, 2128-2138 (Year: 2017).*
Yan et al , Construction of Injectable Double-Network Hydrogels for Cell Delivery, Biomacromolecules, 18, 2028-2038. (Year: 2017).*

* cited by examiner

*Primary Examiner* — Carlos A Azpuru
(74) *Attorney, Agent, or Firm* — Winstead PC

(57) ABSTRACT

A cartilage mimetic gel includes double network hydrogels. The double network hydrogels comprise a first crosslinked network and a second crosslinked network. The first crosslinked network can be formed from poly(2-acrylamido-2-methylpropane sulfonic acid). The second crosslinked network can be formed from poly(N-isopropyl acrylamide-co-acrylamide).

18 Claims, 10 Drawing Sheets

Cross-Section

Non-Porated

Fully-Porated

Perimeter-Porated

Perimeter-Porated
Polydopamine Coated

CARTILAGE MIMETIC GELS

CROSS-REFERENCES TO RELATED APPLICATIONS

This application claims the benefit of priority to and incorporates by reference the entire disclosure of U.S. Provisional Patent Application No. 62/838,131 filed on Apr. 24, 2019.

STATEMENT REGARDING FEDERALLY SPONSORED RESEARCH

This invention was made with government support under M1703014 awarded by the National Science Foundation and under R01DK095101 awarded by the National Institutes of Health. The government has certain rights in the invention.

BACKGROUND

This section provides background information to facilitate a better understanding of the various aspects of the disclosure. It should be understood that the statements in this section of this document are to be read in this light, and not as admissions of prior art.

Articular cartilage provides a robust interface that minimizes friction between bones in load-bearing joints. When this tissue is damaged, it can induce pain, reduced joint movement and potentially lead to degenerative joint disease or osteoarthritis (OA). Although progress has been made towards the treatment of chondral and osteochondral defects, significant challenges remain due to its poor healing capacity. Current treatments for articular cartilage defects include microfracturing, autologous chondrocyte implantation (ACI), and Osteochondral Autograft Transfer System (OATS)(i.e. mosaicplasty).

Microfracturing has shown success in restoring joint function; although, the newly formed fibrocartilage has limited mechanical properties compared to native hyaline cartilage making it susceptible to re-injury. ACI has emerged as a viable method to regenerate hyaline-like cartilage, however it requires an expensive, two-stage procedure. When a more regenerative approach (e.g. microfracturing and ACI) is not applicable, due to damage or disease of the underlying bone, a replacement strategy such as OATS must be taken. Although autografting has a notably high success rate, it suffers from many limitations such as donor site morbidity, defect size ($\sim$1-4 cm$^2$), patient age ($<\sim$50 years) and tissue availability. If these treatments fail, total knee replacement (TKR) is required, which entails a costly, intensive surgery. Currently, the number of TKRs is projected to grow to >3 million procedures by 2030 in the United States alone.

More recently, techniques such as focal resurfacing have developed as a synthetic cartilage replacement of the localized defect area. These BIOPOLY® implants utilize a titanium anchoring pin capped with an UHMWPE-based surface which avoids the biological limitations of autografts and provides a treatment that does not rely on the regeneration of hyaline cartilage. Although studies on focal resurfacing have shown promise so far, the inherent mechanical mismatch between the metallic/hard plastic device and the surrounding osteochondral tissue are associated with complications (e.g. stress-shielding).

Towards improving the treatment of cartilage defects, it is proposed to bridge the gap between focal resurfacing and OATS by developing a cartilage-mimetic, synthetic hydrogel. Conventional hydrogels are not suitable for load-bearing applications due to their relatively poor mechanical properties. For example, CARTIVA® is a commercially available hydrogel-based synthetic cartilage implant composed of poly(vinyl alcohol) (PVA), but it is thus far only FDA-approved for use in the toe joints (i.e. low weight-bearing joints). Remarkable progress was seen with the introduction of double network (DN) hydrogels, which have achieved notable strengths in the MPa range. Although great strides have been made in strengthening hydrogels, most do not exhibit the high moduli and/or water content equal to that of articular cartilage tissue. The development of a hydrogel-based synthetic cartilage has the potential to overcome many limitations of current chondral defect treatments. Many efforts have attempted to replicate the unique characteristics of cartilage in hydrogels, but none simultaneously achieved high modulus, strength and toughness while maintaining the necessary hydration required for lubricity.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

Herein, DN hydrogels, composed of a poly(2-acrylamido-2-methylpropane sulfonic acid) (PAMPS) first network and a poly(N-isopropyl acrylamide-co-acrylamide) (P(NIPAAm-co-AAm)) second network, are evaluated as a potential off-the-shelf material for cartilage replacement. While predominantly used for its thermosensitivity, PNIPAAm is employed to achieve superior mechanical properties and its thermal transition temperature tuned above the physiological range. These PNIPAAm-based DNs demonstrate a 50-fold increase in compressive strength ($\sim$25 MPa, similar to cartilage) compared to traditional single network (SN) hydrogels while also achieving a cartilage-like modulus ($\sim$1 MPa) and hydration ($\sim$80%). By directly comparing to healthy cartilage (porcine), these hydrogels are confirmed not only to parallel the strength, modulus and hydration of native articular cartilage but also exhibit a 50% lower coefficient of friction (COF). The exceptional cartilage-like properties of the PAMPS/P(NIPAAm-co-AAm) DN hydrogels makes them candidates for synthetic cartilage grafts for chondral defect repair, even in load-bearing regions of the body.

In an embodiment, the present disclosure pertains to a cartilage mimetic gel including double network hydrogels, where the double network hydrogels include a first crosslinked network and a second crosslinked network. In some embodiments, the first crosslinked network is formed from poly(2-acrylamido-2-methylpropane sulfonic acid). In some embodiments, the second crosslinked network is formed from poly(N-isopropyl acrylamide-co-acrylamide).

In some embodiments, at least one of the first crosslinked network and the second crosslinked network include a comonomer. In some embodiments, the double network hydrogels include a comonomer, including, but not limited to, a zwitterionic comonomer, a hydrophilic comonomer, a neutral comonomer, or combinations thereof. In some embodiments, at least one of the first crosslinked network and the second crosslinked network include a cross-linker.

In some embodiments, a third crosslinked network having an anionic, cationic, zwitterionic, or neutral charge is added.

In these embodiments, the double network hydrogel is a base for creating a triple network hydrogel.

In some embodiments, the double network hydrogels are porated. In some embodiments, the double network hydrogels are coated with polydopamine. In some embodiments, the double network hydrogels combined with an anchoring base. In some embodiments, the anchoring base is at least one of a regenerative polymeric scaffold, a metal, and an alloy.

In some embodiments, the triple network hydrogels are porated. In some embodiments, the triple network hydrogels are coated with polydopamine. In some embodiments, the triple network hydrogels combined with an anchoring base. In some embodiments, the anchoring base is at least one of a regenerative polymeric scaffold, a metal, and an alloy.

In a further embodiment, the present disclosure pertains to a method of forming a cartilage mimetic gel including irradiating a first network precursor in a first network, forming a single network hydrogel, soaking the single network hydrogel in a second network including a second network precursor, irradiating the second network precursor forming a double network hydrogel structure, and soaking the double network hydrogel structure to allow for the double network hydrogel structure to swell to equilibrium. In some embodiments, the first network is formed from poly(2-acrylamido-2-methylpropane sulfonic acid). In some embodiments, the second network is formed from poly(N-isopropyl acrylamide-co-acrylamide). In some embodiments, at least one of the first network and the second network include a comonomer. In some embodiments, the double network hydrogel includes a comonomer, including, but not limited to, a zwitterionic comonomer, an anionic comonomer, a cationic comonomer, a hydrophilic comonomer, a neutral comonomer, or combinations thereof. In some embodiments, at least one of the first network and the second network include a cross-linker.

In some embodiments, the method further includes porating the double network hydrogel. In some embodiments, the method further includes coating the double network hydrogel with polydopamine. In some embodiments, the method further includes combining the double network hydrogel with an anchoring base. In some embodiments, the anchoring base is at least one of a regenerative polymeric scaffold, a ceramic, a metal, and an alloy.

BRIEF DESCRIPTION OF THE DRAWINGS

A more complete understanding of the subject matter of the present disclosure may be obtained by reference to the following Detailed Description when taken in conjunction with the accompanying Drawings wherein:

(FIG. 3D) shows representative stress vs. strain curves showing the compressive behavior at both small (inset) and large strains. All *'s indicate statistical significance from cartilage unless otherwise denoted, in which "*" represents p<0.05, "*" represents p<0.001 and "**" represents p<0.0001.

DETAILED DESCRIPTION

Figure 1:
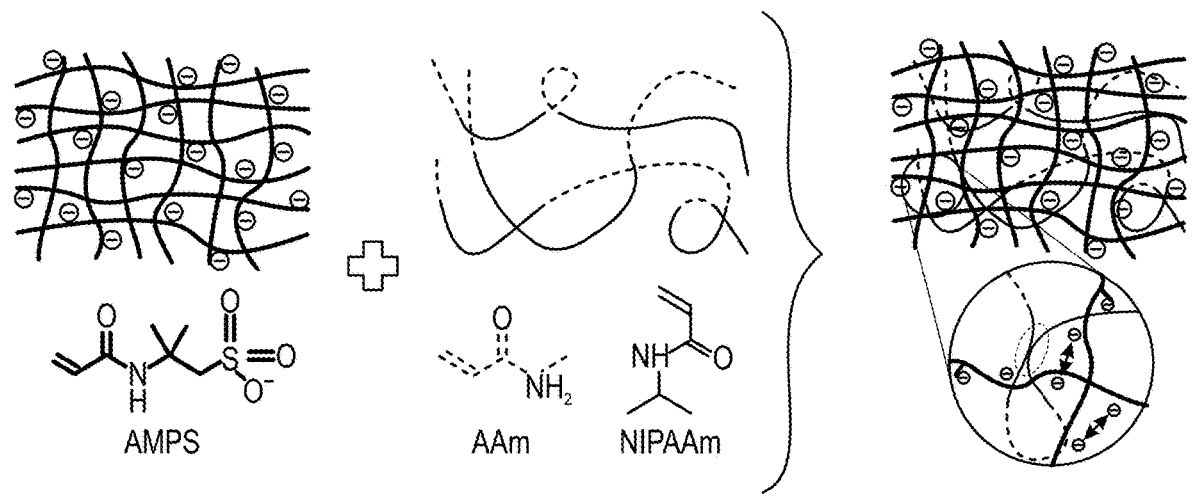
FIG. 1 illustrates non-thermoresponsive PAMPS/P(NIPAAm-co-AAm) DN hydrogels formed with an anionic PAMPS first network and a tunable, thermoresponsive second network comprised of NIPAAm copolymerized with AAm. Inset: Ionic interactions (arrows) within first network and reversible hydrophobic interactions (dotted circles) within the second network.

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

Due to their poor healing capacity, cartilage defects are commonly treated using autografts which frequently suffer from donor site morbidity and are limited by the defect size. Hydrogels could potentially be useful as a synthetic alternative to autografts due to their similarity in structure to extracellular matrix (ECM). However, hydrogels are severely limited by their deficient mechanical properties. In particular, simultaneous achievement of high strength and stiffness for hydrogels is quite uncommon. As such, the present disclosure relates to hydrogels with potential for cartilage replacement that are prepared by employing a DN design of a tightly crosslinked, highly negatively charged first network based on poly(2-acrylamido-2-methylpropane sulfonic acid) and a loosely crosslinked second network based on thermoresponsive N-isopropylacrylamide (NIPAAm) copolymerized with zwitterionic [2-(methacryloyloxy)ethyl]dimethyl-(3-sulfopropyl)ammonium hydroxide (MEDSAH) or neutral acrylamide (AAm). Notably, the DN hydrogels disclosed herein are able to mimic the modulus, strength, lubricity, and hydration of articular cartilage making them promising candidates for synthetic cartilage grafts. In addition to their cartilage-mimetic properties, DN hydrogels may optionally exhibit a highly tailorable, thermally triggered volume change to assist in self-fitting into the defect site, which can be optionally tuned out of the physiologic range with the addition of AAm. The relatively simple preparation of DN hydrogels allows for their fabrication in a variety of geometries to easily match the required size of a cartilage defect.

Furthermore, these cartilage mimetic hydrogels can optionally be used in conjunction with another material, such as a regenerative scaffold (e.g. hydrogel and non-hydrogels) or a metal (e.g. titanium, stainless steel) serving as an anchoring device or "base". To further enhance tissue integration with surrounding cartilage, DN hydrogels may be porated either throughout the material or solely around the perimeter nearest the tissue interface. Alternatively, or in conjunction with poration, a polydopamine coating may be applied to all or part of the cartilage mimetic gel to promote tissue adhesion and integration.

DN Hydrogel Structure. DN hydrogels, a subset of interpenetrating network (IPN) hydrogels, include two asymmetrically cross-linked networks that can optionally be ionically charged. For example, a first network is tightly crosslinked and negatively charged, and a second network that is loosely crosslinked and neutral, or zwitterionic, can be utilized.

Chemical Composition of DN Hydrogels. First Network: poly(2-acrylamido-2-methylpropane sulfonic acid), N,N'-methylenebisacrylamide (BIS, cross-linker), 2-oxoglutaric acid (UV-initiator), and deionized water (DI). Second Network: N-isopropylacrylamide (NIPAAm) with optional comonomers including [2-(methacryloyloxy)ethyl]dimethyl-(3-sulfopropyl)ammonium hydroxide (MEDSAH; "zwitterionic comonor") and acrylamide (AAm; "neutral, hydrophilic comonomer"), N,N'-methylenebisacrylamide (BIS, cross-linker), 2-oxoglutaric acid (UV-initiator), and DI. In some embodiments, other zwitterionic, anionic, cationic, neutral, or hydrophilic comonomers, cross-linkers, and imitators may be substituted.

Fabrication Method. Sequential UV Curing: The first network hydrogel is formed through UV-irradiation of a first network precursor solution within a transparent mold to form a SN hydrogel. This SN hydrogel is then soaked in a second network precursor solution until reaching equilibrium and transferred into a second mold for additional UV-irradiation. After curing, the DN hydrogel is soaked in DI to remove any unreacted moieties and allowed to swell to equilibrium.

To porate the cartilage mimetic hydrogels (at the tissue-contacting perimeter), a porogen (e.g. thermoplastic porogen) is added during the first UV-cure step to all, or part, of the mold which remains present until the DN hydrogel is fully formed. Interconnectivity of pores can optionally be achieved through annealing to lightly fuse the porogens together. Then, the porogens are removed from the DN hydrogels via soaking the porogens in a solvent to induce dissolution, producing pores with tunable size (e.g. ~100 microns) and potential interconnectivity to promote adjacent chondral tissue integration into the hydrogel. In some embodiments, a third network cures around a template that is subsequently dissolved, the removal of which leaves a porous structure behind.

To coat the hydrogel with polydopamine, either all or part of the DN hydrogel is submerged within a dopamine solution (e.g. dopamine hydrochloride for 24 hours). If used in conjunction with poration, the polydopamine coating is applied after the porogens have been removed.

This fabrication process allows for high tunability of size and geometry, tunable pore size and interconnectivity through selected porogens, and provides for a simple coating technique that can be applied directly to the hydrogel material. Additionally, no post-processing of the materials is necessary, no harsh chemicals are needed for synthesis or as curing agents, and heat is not required heat for curing (which can negatively affect thermosensitive materials), NIPAAm-Based DN Hydrogels. Previously, the appropriate combination of stiffness, strength, and hydration has not been achieved to successfully mimic natural cartilage. The use of NIPAAm as the second network of these DN hydrogels is unique because it is not only being utilized for its thermosensitivity, but also for its ability to enhance the modulus of these hydrogels without reducing their water content. These DN hydrogels are the first to exhibit cartilage-like stiffness, strength, and hydration.

Thermoresponsive, Zwitterionic DN Hydrogels. The addition of a zwitterionic comonomer, MEDSAH, into the NIPAAm second network produced unique results in mechanical properties without affecting the thermosensitivity. The ability of this DN hydrogel to achieve a high modulus while simultaneously reaching remarkably high strengths is unlike any previously reported hydrogels. The main contributor to this enhancement are new inter-/intra-network ionic interactions that are introduced between MEDSAH (zwitterionic) in the second network and AMPS (anionic) in the first network. These reversible ionic interactions result in a higher modulus under low stresses in the elastic region while providing a route for stress dissipation through breakage of these ionic bonds at higher stresses.

Non-Thermoresponsive DN Hydrogels. The addition of a neutral, hydrophilic comonomer, AAm, into the NIPAAm second network allows for tunability of the VPTT while enhancing the fracture strength. AAm has been used to adjust the transition temperature of NIPAAm SN hydrogels, but has not previously been used for this reason in DN hydrogels. By raising the transition temperature above physiologic range, these ultra-strong DN hydrogels exhibit mechanical stability within the body for use as non-thermosensitive implants.

Perimeter Poration. The use of a porogen within a DN hydrogel to spatially control pore size and interconnectivity is a significant enhancement towards ultra-strong hydrogels capable of integration with the surrounding tissue. In some embodiments, poration may include poration through a third network. Most DN hydrogels are non-porous, with mesh sizes in the 1-10's nm range, which does not allow for the migration of cells into the material.

Polydopamine Coating. The use of polydopamine as a tissue adhesion promoter has previously shown promise. This coating has not been previously been applied to DN hydrogels, making this a unique combination of both replacement and regenerative approaches to achieve successful tissue integration.

Connection with an Anchoring Base. The combination of a cartilage replacement material in conjunction with an anchoring base is important for long-term stability. Examples of potential "bases" are regenerative, polymeric scaffolds, ceramics, and metals/alloys. In some embodiments, a porous regenerative hydrogel scaffold provides a method to regenerate the underlying bone while the cartilage mimetic DN immediately supports mechanical loads after implantation. Alternatively, the use of a titanium pin as a base has been used in CE marked BIOPOLY™ resurfacing implants. By utilizing this established anchoring pin with our cartilage mimetic hydrogel, the strength, modulus, and hydration of cartilage compared to current resurfacing techniques can be matched.

Synthetic Cartilage Grafts. The DN hydrogels, porated or non-porated, can conveniently be fabricated as autograft-sized plugs for facile translation into commonly performed autografting procedures, such as, but not limited to, OATS. OATS is a well-established autografting procedure, providing the ideal platform for adaptation to a synthetic hydrogel implant. Notably, utilizing a synthetic graft will shorten the current procedure significantly by eliminating the harvesting step and limitations that follow, such as donor site morbidity and limitations on defect size. Ultimately, this adapted-OATS procedure would include two main steps: clearance of the damaged cartilage and bone via a cylindrical coring device and insertion of the synthetic hydrogel graft. The DN hydrogels may also be use in conjunction with allograft procedures and may be provided in a variety of shapes and sizes.

Optionally, the cartilage mimetic hydrogel, porated or non-porated, can be formed as a thin layer on top of a porous regenerative hydrogel scaffold. Similarly, this two-part hydrogel implant can be fabricated as autograft-sized plugs for direct translation into the well-established OATS procedure. This design enhances the integration of the implant with the surrounding osteochondral tissue.

More recently, ultra-high molecular weight polyethylene (UHMWPE) capped titanium (Ti) screws have been developed as synthetic alternatives to autografting, known as focal knee resurfacing implants. One upcoming product that has been commercialized within the last decade is the BIOPOLY™ RS Partial Resurfacing Knee Implant. These devices are currently CE marked for use in most international markets and still seeking IDE approval for use in the United States. Results thus far look promising. However, it is widely known that UHMWPE can produce harmful wear debris over time. Additionally, UHMWPE fails to match many of the basic properties of articular cartilage, including but not limited to the water content and stiffness. Therefore, an aspect of the present disclosure involves the replacement of the UHMWPE cap with DN hydrogels on these Ti screw implants. Advantageously, the procedure for implantation would not require any adjustments from the currently established methods for these implants, such as the BIOPOLY™.

Current Procedures. In the OATS procedure, healthy tissue is harvested from undamaged regions of the knee in the form of cylindrical autografts and transferred to pre-drilled sites in the defect area. However, the requirement to harvest healthy tissue from the patient is a major disadvantage of autograft-based procedures. It not only limits the size of defect that can be treated, but also can lead to donor site morbidity due to damage caused by the harvesting procedure. Additionally, many patients lack sufficient healthy tissue for donation, therefore must seek alternative treatment methods.

Microfracture: To promote healing of the cartilage defect, microfractures are made in the exposed bone to release bone marrow stem cells (BMSCs) to facilitate chondrogenesis. However, the results are inconsistent due to the formation of fibrocartilage in place of the native hyaline cartilage. Fibrocartilage does not exhibit the same mechanical properties and can lead to re-injury of the defect site.

Autologous Chondrocyte Implantation: ACI is a recently approved alternative method to promote healing of articular cartilage defects that requires a two-stage procedure. First, chrodocytes are harvested from the patient and expanded for 6-8 weeks to produce a large enough quantity of the cells for implantation. Second, a small patch is sewn over the articular cartilage defect and the expanded chondrocytes are injected underneath to regenerate the native hyaline cartilage. However, the complex, two-stage procedure requires time for the patient's cells to be expanded as well as to regenerate after implantation, resulting in a lengthy and expensive procedure.

Focal Knee Resurfacing: A synthetic autograft alternative has been developed. However, it has not obtained IDE approval in the United States. This focal knee-resurfacing device, BIOPOLY™, is generally an ultra-high molecular weight polyethylene (UHMWPE) capped Ti screw that can be implanted in the defect site to replace the damaged cartilage. However, the current materials used in focal resurfacing devices (Ti and UHMWPE) exhibit a significant mechanical mismatch from the native tissue. This potentially can lead to implant loosening and failure of the device. Additionally, UHMWPE has been shown to produce harmful wear debris in previous TKR implants; although, this has not been seen thus far in the focal resurfacing implants.

Total Knee Replacements: If none of the aforementioned procedures are available for the patient, a TKR is necessary. This surgery involves the complete removal of the injured knee joint and replacement with a prosthetic knee, most commonly including a Ti stem and an UHMWPE articulating surface. However, TKRs are costly and more intensive procedures than the aforementioned. Moreover, the lifetime of a TKR implant is commonly less than the lifespan remaining of the patient, resulting in the need for additional TKR procedures later in life. Also, the use of UHMWPE as the articulating surface has the potential to create harmful wear debris.

In view of the above current procedures, a synthetic cartilage hydrogel, such as those disclosed herein, avoid donor site morbidity, eliminates limits on defect size, avoids long, multi-step, procedures, achieves more similar properties to native hyaline cartilage than fibrocartilage or UHMWPE, and provide a less expensive, longer-lasting, option than TKRs.

In some embodiments, cartilage mimetic DN hydrogels can be fabricated as bulk sheets and punched into autograft size cylinders. In some embodiments, such a DN can be combined with an "anchoring device/base" (e.g. polymeric regenerative scaffold or metal) to form autograft-size or other shaped devices suitable for implantation. In some embodiments, the resulting devices can be sealed in a pouch for sterilization and shipping. In some embodiments, the pouch could contain water or buffer solution to maintain hydration until use. In some embodiments, such devices would represent off-the-shelf alternatives to autografting, focal resurfacing, and other clinical procedures. Additionally, in some embodiments of the present disclosure, this synthetic hydrogel graft can be used in humans and animals (e.g. canine, equine) to treat chondral and osteochondral defects through an adapted-autograft procedure.

Working Examples

Reference will now be made to more specific embodiments of the present disclosure and data that provides support for such embodiments. However, it should be noted that the disclosure below is for illustrative purposes only and is not intended to limit the scope of the claimed subject matter in any way.

The inability of hydrogels to simultaneously mimic the strength, modulus and hydration of cartilage was tested, wherein the properties of native porcine articular cartilage tested was compared to previously reported ultra-strong hydrogels. Mimicking the native cartilage deformation/recovery response is also important to avoid any imbalance in contact stress surrounding the synthetic implant. Thus, beyond the general mechanical properties such as modulus and strength, similar viscoelastic behavior and lubricity is essential for a synthetic cartilage material. Typical ultra-strong hydrogels, due to their low moduli exhibit much greater deformation than cartilage at a similarly applied stress. This mechanical mismatch can lead to stress concentration at the defect edges and potentially failure of the implant-tissue interface. Additionally, the primary function of cartilage tissue is to provide a lubricious surface to minimize friction during reticulation of joints.

Although hydrogels are known as a class of materials with high lubricity, current methods to enhance their compressive modulus typically result in a decrease in water content and a subsequent reduction in lubricity. To overcome this, one approach utilized a bilayer hydrogel design with a robust, low water content region and a lubricious, high water content region with reduced mechanical properties as the low friction surface. However, the cartilage-mimetic DN hydrogel reported herein is intended to achieve all requisite properties, including strength, modulus, hydration and lubricity without the need for a bilayer system that could suffer from delamination or damage to the soft, lubricious layer.

It has been demonstrated that DN hydrogels can simultaneously achieve both high strength (~23 MPa) and high stiffness (~1.5 MPa) without compromising water content (>80%). These membranes included tightly crosslinked, anionic poly(2-acrylamido-2-methylpropane sulfonic acid) network interpenetrated by a loosely crosslinked, zwitterionic poly(N-isopropylacrylamide-co-[2-(methacryloyloxy)ethyl] dimethyl-(3-sulfopropyl) ammonium hydroxide) [P(NIPAAm-co-MEDSAH)] network that utilized intra- and inter-chain electrostatic interactions to enhance the compressive mechanical properties. Due to PNIPAAm's thermosensitivity, such DN hydrogels with VPTT ~35° C. would experience shrinkage upon implantation as a synthetic cartilage graft and would not statically remain in a fully swollen state due to local temperature fluctuations. This dimensional instability could potentially cause implant loosening with variations in local body temperature.

Herein, cartilage-mimetic DN hydrogels composed of asymmetrically crosslinked networks of PAMPS and NIPAAm copolymerized with acrylamide (AAm) [P(NIPAAm-co-AAm)] have been developed. The VPTTs of the DNs were progressively tuned above normal physiologic temperatures, establishing dimensional stability in a physiological environment (i.e. a lack of deswelling/reswelling). Notably, NIPAAm was utilized for its ability to enhance the stiffness of the DN hydrogels rather than its prominent use as a thermosensitive polymer. This stiffening phenomenon has been demonstrated previously in AAm-based semi-interpenetrating network (semi-IPN) hydrogels, in which physical interactions between the PNIPAAm chains were shown to increase the apparent crosslink density and thus, stiffness at all temperature ranges (i.e. above and below the VPTT). As discussed in further detail below, key properties of the PAMPS/P(NIPAAm-co-AAm) DNs, including water content, modulus, strength and toughness, were evaluated to determine their potential as synthetic cartilage candidates. Additionally, the viscoelastic behavior of the DN hydrogels was analyzed through observing the creep response to an applied load. Finally, the coefficient of friction (COF) was measured to determine the lubricity of the hydrogels. To enable a direct comparison, all mechanical testing was likewise performed on harvested articular cartilage (porcine). Through the material design and subsequent testing, the goal of this work was to develop a material that closely mimics native cartilage to act as a synthetic replacement strategy to avoid the disadvantages of current autografting treatments as well as the large mechanical mismatch of recent focal resurfacing techniques.

Materials. N-Isopropylacrylamide (NIPAAm, 97%), 2-acrylamido-2-methylpropane sulfonic acid (AMPS, 97%), acrylamide (AAm, >99%), 3-(acrylamidopropyl)trimethylammonium chloride solution (AAPTAC, 75 wt % in $H_2O$), N,N'-methylenebisacrylamide crosslinker (BIS, 99%) and 2-oxoglutaric acid photo-initiator, sodium azide (≥99.5%) and ethylene-diaminetetraacetic acid (EDTA) disodium salt dihydrate were obtained from Sigma-Aldrich. For hydrogel fabrication, deionized water (DI) with a resistance of 18 MΩ·cm (Cascada LS MK2, Pall) was used. Phosphate-buffered saline (PBS, 1X, pH 7.4, without calcium and magnesium), lactate dehydrogenase (LDH) cytotoxicity assay kit (PIERCE™) and fetal bovine serum (FBS, Hyclone) were obtained from Fisher Scientific. Antibiotic solution (100X) (stabilized bioreagent sterile filtered with 10,000 units of penicillin and 10 mg of streptomycin per mL), sodium bicarbonate ($NaHCO_3$) and Dulbecco's Modified Eagle's Medium (DMEM) (1000 mg $dL^{-1}$ glucose and L-glutamine without $Na_2CO_3$ and phenol red) were purchased from Sigma-Aldrich. Mesenchymal progenitor cells C3H/10T1/2, Clone 8 (CCL226™) were obtained from the American Type Culture Collection (ATCC®).

DN Hydrogel Fabrication. DN hydrogels were fabricated through a two-step, UV-cure process in which single network (SN) hydrogels are soaked in a second network precursor solution and subsequently cured to form an interpenetrating network hydrogel. The SN precursor solutions consisted of AMPS (1.5 M), BIS crosslinker (4 mol %) and 2-oxoglutaric acid (0.1 mol %) in DI water. The precursor solution was injected between two glass slides separated by 1 mm thick spacers and exposed to UV light (UV-transilluminator, 6 mW $cm^{-2}$, 365 nm) for 5 hours while rotated at standard intervals to maintain symmetry. The SN hydrogel was removed from the mold and immediately immersed in the DN precursor solution for 48 hours at 4° C. The DN precursor solution consisted of NIPAAm (2.0 M), BIS (0.1 mol %) and 2-oxoglutaric acid (0.1 mol %) in DI water with varying amounts of a hydrophilic comonomer (AAm, 0-15 wt % w.r.t. NIPAAm). After soaking, the hydrogel was enclosed with two glass slides separated by spacers (~1.25 mm) to form a complete seal (i.e. no air space) and then exposed to UV light for 5 hours while submerged in an ice bath (~7° C.) and rotated at standard intervals. The resulting DN hydrogels were then removed from the molds and soaked in DI water for one week before testing. As supplementary controls, anionic AMPS, cationic AAPTAC or additional NIPAAm were incorporated at 10 wt % w.r.t. NIPAAm as comonomers in the second network instead of comonomer and prepared similarly. Finally, an AAm-only control was also prepared similar to the "DN-AAm-0%" with a 1.5 M AMPS first network and a 2.0 M AAm second network (i.e. no NIPAAm).

Equilibrium Water Content. The values for equilibrium water content were calculated as $[(Ws-Wd)/Ws] \times 100$, where Ws was the swollen weight of the hydrogel or cartilage disc and Wd was the dry weight of the hydrogel or cartilage disc after exposure to high vacuum at 60° C. overnight.

VPTT. Differential scanning calorimetry (DSC, TA Instruments Q100) was used to determine the VPTT of swollen DN hydrogels. A small square hydrogel specimen (~10 mg, cut with a razor blade) was blotted dry with a Kim Wipe and sealed in a hermetic pan. The sample was first cooled to 0° C. then the temperature was ramped up to 65° C. and back down to 0° C. at a rate of 3° C. per minute for two continuous cycles. The VPTT was characterized by the peak temperature of the endotherm (Tmax) and the initial temperature at which the endothermic phase transition peak starts (To). Reported data are from the second heating cycle to ensure any thermal history has been erased and to simulate an arbitrary nth heating cycle.

Tension. The tensile mechanical properties were evaluated with an Instron 3340 at RT. Hydrogels were punched into 3 dog-bone specimens (3 mm width, ~30 mm gauge length) with a die. Each sample was blotted with a Kim Wipe to remove surface water and then placed in the tensile clamps with an initial pre-load force of 0.2 N. The hydrogels were tested at a constant strain rate of 10 mm/min until fracture. The elastic tensile modulus (E) was obtained from the slope of the linear portion of the stress-strain curve (0-10% strain). The ultimate tensile strength ($\sigma f$) and the % strain at break ($\epsilon f$) was defined respectfully as the stress and strain values at the point of fracture.

Static Compression. The compressive mechanical properties, including elastic modulus and strength, were evaluated with an Instron 3340 at RT. Hydrogels were punched into 3 discs (6 mm×~2 mm, diameter×thickness) with a 6 mm biopsy punch. Healthy porcine articular cartilage was harvested from humeral condyles obtained within 24 hours after slaughter from the Rosenthal Meat Science and Technology Center at Texas A&M University. Using a 6 mm biopsy punch, cartilage discs (~6 mm×~1-2 mm, diameter×thickness) were removed from the bone and tested immediately. All cartilage samples were never frozen before testing to avoid damage and/or dehydration that could lead to reduced mechanical performance. Each hydrogel and cartilage disc was blotted to remove surface water and then placed between the parallel plates with an initial pre-load force of 0.5 N. The samples were compressed at a constant strain rate of 1 mm/min until fracture. The elastic compressive modulus (E) was obtained from the slope of the linear portion of the stress-strain curve (0-5% strain). The ultimate compressive strength ($\sigma_f$) and the % strain at break ($\epsilon_f$) were defined respectfully as the stress and strain values at the point of fracture. Finally, the toughness ($U_t$) was obtained from the integration of the stress-strain curve.

Creep. A dynamic mechanical analyzer (DMA) was utilized to examine the creep response of the DN hydrogels and porcine cartilage to compare their viscoelastic behavior. Discs of each specimen type were prepared as in static compression testing (6 mm×~2 mm, diameter×thickness). Creep strain was recorded over time to evaluate the instantaneous strain and final creep strain reached after 1 hour of loading under a constant load of 0.35 MPa. Recovery % from maximum strain value after 1 hour of creep compression was reported immediately after removal of the load as well as 30 minutes after removal of load to observe differences in recovery rates.

Lubricity. The coefficient of friction (COF) was examined through tribology using a simulative synovial fluid lubricant comprised of fetal bovine serum (FBS) diluted with DI (60% v/v) to a protein content of ~20 g/L with 0.2 w/v % sodium azide (antibacterial) and 20 mM ethylene-diaminetetraacetic acid (EDTA) disodium salt dehydrate (chelating agent), adopted from ASTM F732 'Standard Test Method for Wear Testing of Polymeric Materials Used in Total Joint Prostheses'. Hydrogel and cartilage specimens were soaked in the FBS solution then clamped into the base of the tribometer chamber and fully covered with FBS. The indenting pin, alumina ball (ø~6 mm), was articulated at 20 mm/s in a straight line reciprocating motion of ~10 mm in length. The COF was determined at 300 reciprocating cycles or after reaching equilibrium. The mean Hertzian contact pressure was calculated as ~0.6 MPa with an applied load of 5 N. Average joint peak stresses range from ~0.1 to 5.0 MPa, thus the contact pressure used was within the physiologic range.

Cytocompatibility. DN hydrogel cytocompatibility was assessed by measuring LDH concentrations released by mouse mesenchymal progenitor 10T1/2 cells 24 hours after cell seeding onto the hydrogel specimens versus tissue culture plastic (i.e. polystyrene, PS). Four hydrogel discs of each composition were punched (8 mm×~2 mm, diameter× thickness) and sterilized by two changes of ethanol/water (70/30; 45 minutes). The discs were then transferred to a sterile 48-well plate and washed with sterile PBS (3×30 minutes) then immersed in sterile PBS for 48 hours (PBS exchanged at 24 hours). Next, 10T1/2 cells suspended in DMEM (without phenol red) supplemented with 10% FBS and 1% PS were seeded onto each hydrogel disc and also into four empty tissue culture plastic wells at a concentration of ~6000 cells $cm^{-2}$. Cells were incubated for 24 hours at ~37° C. with 5% $CO_2$. Finally, media was collected from each well and assessed for LDH level per the manufacture's protocol (Pierce™). The relative LDH activity was calculated by normalizing to the absorption of PS.

Statistics. For all tension, static compression, lubricity and cytocompatibility testing, statistical analysis values were compared using one-way ANOVA with Dunnett's correction to determine p-values. For creep recovery, statistical analysis values were compared using 2-way ANOVA with Tukey's correction to determine p-values.

Figure 2:
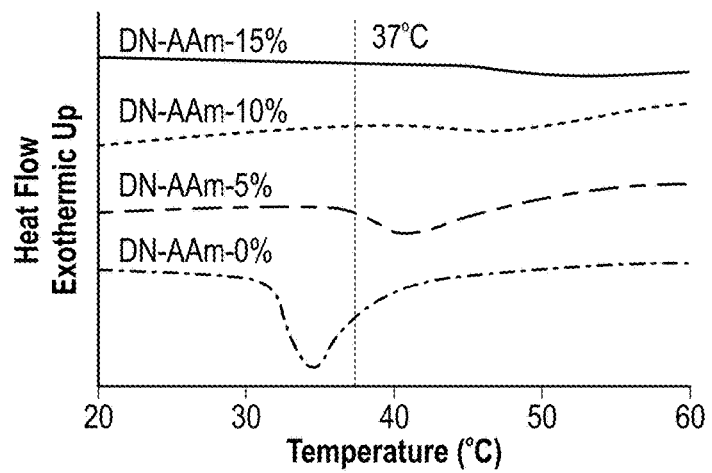
FIG. 2 illustrates DSC thermograms of the PAMPS/P(NIPAAm-co-AAm) DN hydrogel series showing the shift of the volume phase transition temperatures (VPTT) with increasing AAm in the second network. With 10 wt % AAm, the onset of the thermal transition can be tuned well above the physiologic range (Tonset >37° C.).

The PAMPS/P(NIPAAm-co-AAm) DN hydrogels were fabricated in a two-step UV-cure method (FIG. 1) with compositions denoted as "DN-AAm-X %" where X represents the wt % of AAm copolymerized into the second network (5, 10 or 15 wt % based on NIPAAm) (Table 1). An SN control, composed only of the first network, as well as a DN control, containing no AAm in the second network, were also prepared. For all DN hydrogels, a 1.5 M AMPS first network and a 2.0 M NIPAAm second network were maintained as this was previously optimized for the best combination of high modulus and high strength. However, with no further modification, dimensional instability (i.e. thermally driven cyclical deswelling/reswelling) would occur with body temperature fluctuations, making it an unsuitable candidate as a synthetic cartilage replacement. Therefore, by the addition of a hydrophilic comonomer (i.e. AAm) to the PNIPAAm second network, the VPTT of the resulting DN was shown to be successfully tuned above the physiologic range (>40° C.) with as little as 10 wt % AAm (Table 1, FIG. 2). This is attributed to the increased hydrophilicity of the P(NIPAAm-co-AAm) network requiring greater thermal energy to disrupt hydrogen bonding and to subsequently permit hydrophobic interactions to dominate between the isopropyl groups of NIPAAm. Such tunability of the VPTT via copolymerization with a hydrophilic comonomer has been demonstrated previously in conventional and DN hydrogels. These PNIPAAm-based DN hydrogels could potentially be utilized as a synthetic cartilage replacement and were further evaluated versus healthy cartilage (porcine) as a direct comparison. Table 1 illustrates DN hydrogels detailing first network and second network compositions as well as their thermal transitions (VPTTs).

TABLE 1

| Hydrogel Type | First Network* AMPS(X) | Second Network* NIPAAm | AAm(Y) (wt % of NIPAAm) | VPTT $T_0$(° C.) | $T_{max}$(° C.) |
|---|---|---|---|---|---|
| PAMPS SN: | | | | | |
| SN-AAm-0% | 1.5M | — | — | — | — |
| PAMPS/PNIPAAm DN: | | | | | |
| DN-AAm-0% | 1.5M | 2.0M | 0 wt % | 32.8 ± 0.17 | 35.4 ± 0.22 |
| PAMPS/(PNIPAAm-co-AAm) DNs: | | | | | |
| DN-AAm-5% | 1.5M | 2.0M | 5 wt % | 37.4 ± 0.33 | 41.6 ± 0.07 |
| DN-AAm-10% | 1.5M | 2.0M | 10 wt % | 41.4 ± 0.68 | 48.0 ± 0.19 |
| DN-AAm-15% | 1.5M | 2.0M | 15 wt % | 45.5 ± 0.25 | 52.6 ± 0.77 |

*4 mol % BIS crosslinker, 0.1 mol % 2-oxoglutaric acid initiator †0.1 mol % BIS crosslinker, 0.1 mol % 2-oxoglutaric acid initiator A major challenge of achieving cartilage-like properties is maintaining high water content while attaining the requisite mechanical properties (e.g. modulus, strength and toughness). Since the extent of hydration greatly impacts the lubricity of a surface, it was crucial that the equilibrium water content (EWC) of the DN hydrogels was similar to that of the cartilage. Notably, the water content of all the DN compositions (~80-85%) was slightly higher than the cartilage (~75%), in contrast to current resurfacing strategies utilizing UHMWPE-based coatings which have minimal water content. This ability to mimic the hydration of native cartilage to not only enhance the lubricity, but also the durability and biocompatibility of the device long-term is expected.

Figure 3A:
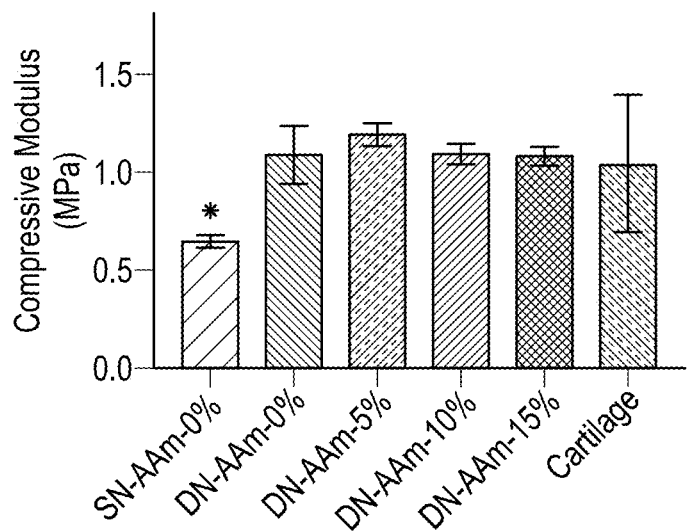
FIGS. 3A, 3B, 3C and 3D show compressive mechanical properties of the PAMPS/P(NIPAAm-co-AAm) DN hydrogel series alongside porcine articular cartilage demonstrating the high modulus (FIG. 3A), high strength (FIG. 3B) and toughness (FIG. 3C) with incorporation of AAm in the second network.
Figure 3B:
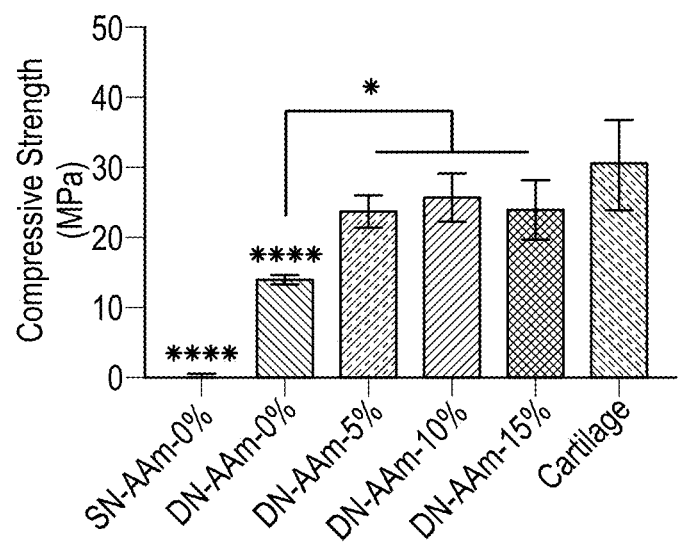
Figure 3C:
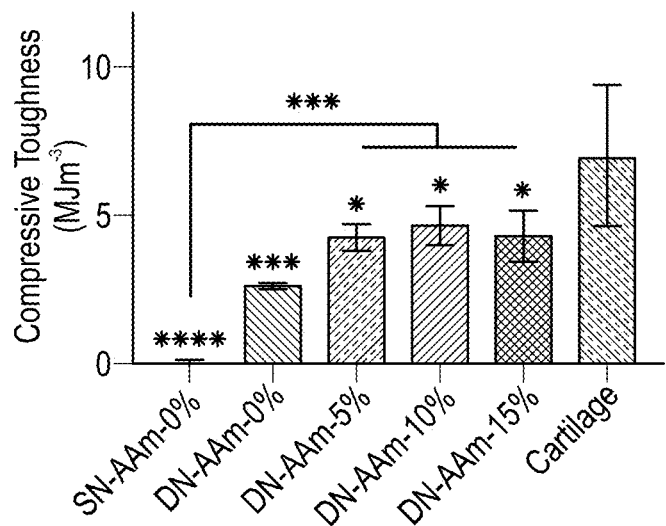
Figure 3D:
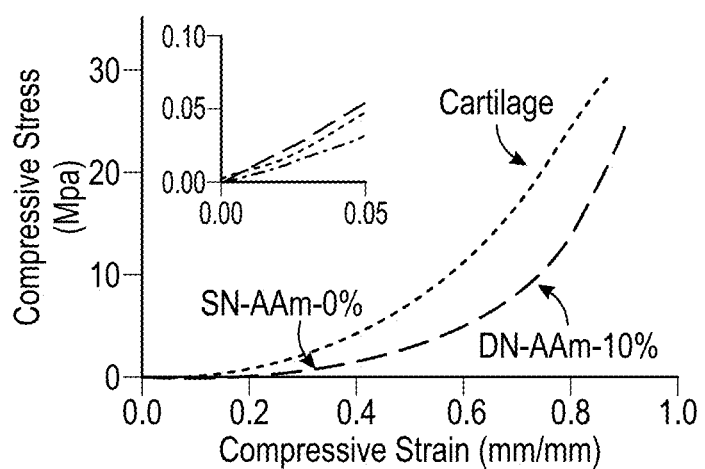

Currently, hydrogels exhibiting high water contents (>~70%) have not been able to achieve both cartilage-like stiffness and strength simultaneously. The reported values for compressive properties of articular cartilage widely vary (e.g. compressive modulus (E) ranges from ~0.5 to 60 MPa) due to large variations in biological tissue and experimental methods. Thus, in this work, porcine articular cartilage was harvested from fresh (i.e. non-frozen) humeral condyles and tested alongside the DN hydrogels to permit direct comparison. In previous studies of DN hydrogels, the introduction of a second, interpenetrating network dramatically increased the compressive strength and toughness versus conventional SN hydrogels; however, their moduli typically remain in the sub-MPa range. In contrast, the unique combination of a PAMPS first network and PNIPAAm second network demonstrated not only an increase in strength and toughness but also in modulus when compared to the PAMPS SN control (i.e. "SN-AAm-0%", FIGS. 3A-3D, Table 2). This increase in stiffness could be attributed to reversible, sacrificial bonds between the hydrophobic groups of PNIPAAm (FIG. 1) enhancing the apparent crosslink density at low strains. Furthermore, the incorporation of just 5-15 wt % AAm into these DN hydrogels significantly enhanced the compressive strength compared to "DN-AAm-0%" (i.e. no AAm; FIG. 3B) while maintaining comparably high compressive moduli (>1 MPa, FIG. 3A), similar to that of the harvested cartilage (~1 MPa, FIG. 3A). Notably, the "DN-AAm-10%" displayed a compressive strength >25 MPa, a substantial increase versus "DN-AAm-0%" (~14 MPa, FIG. 3B). Although the cartilage exhibited a slightly higher average compressive strength (~30 MPa), all AAm-containing DN hydrogels were not statistically lower due to the variability exhibited by the cartilage. In addition, these DNs exhibited a compressive fracture toughness (>4 MJ m$^{-3}$) approaching that of the cartilage (~7 MJ m$^{-3}$, FIG. 3C). Finally, it should be noted that the DN hydrogels sustained greater percent strains before fracture than the cartilage, as demonstrated by the representative stress vs. strain curves (FIG. 3D). The ability of these double networks to reach such high strains (>80%) before failure could improve durability at common contact stresses and strains experienced during normal activity (~0.1-2.0 MPa, ~10-30% strain) as well as at less frequent peak contact stresses (~2-10 MPa).

Table 2, shown below, illustrates Overall mechanical properties of the PAMPS/PNIPAAm-co-AAm) hydrogel series, including equilibrium water content; tensile modulus, strength and fracture strain; and compressive modulus, strength, fracture strain and toughness.

TABLE 2

| | EWC (%) | Tensile Properties | | | Compressive Properties | | | |
|---|---|---|---|---|---|---|---|---|
| | | E (MPa) | σ (MPa) | ε (%) | E (MPa) | σ (MPa) | ε (%) | $U_t$ (MJ m$^{-3}$) |
| PAMPS SN: | | | | | | | | |
| SN-AAM-0% | 96.55 ± 0.00 | 0.33 ± 0.046 | 0.04 ± 0.02 | 10.8 ± 4.1 | 0.65 ± 0.02 | 0.54 ± 0.1 | 34.4 ± 0.8 | 0.07 ± 0.01 |
| PAMPS/PNIPAAm DN: | | | | | | | | |
| DN-AAm-0% | 86.3 ± 0.17 | 1.00 ± 0.04 | 1.61 ± 0.04 | 147.8 ± 9.2 | 1.09 ± 0.14 | 14.1 ± 0.5 | 78.8 ± 1.8 | 2.63 ± 0.07 |
| PAMPS/(PNIPAAm-co-AAm) DNs: | | | | | | | | |
| DN-AAm-5% | 83.9 ± 0.11 | 1.04 ± 0.05 | 1.57 ± 0.06 | 139.4 ± 13.7 | 1.19 ± 0.06 | 23.7 ± 2.4 | 86.9 ± 1.9 | 4.31 ± 0.48 |
| DN-AAm-10% | 83.9 ± 0.21 | 1.13 ± 0.06 | 1.54 ± 0.12 | 128.0 ± 20.5 | 1.09 ± 0.05 | 25.8 ± 3.5 | 90.8 ± 2.6 | 4.69 ± 0.68 |
| DN-AAm-15% | 83.5 ± 0.16 | 1.15 ± 0.09 | 1.53 ± 0.04 | 131.0 ± 13.1 | 1.08 ± 0.04 | 24.1 ± 4.2 | 89.9 ± 3.1 | 4.39 ± 0.80 |

TABLE 2-continued

| | EWC | Tensile Properties | | | Compressive Properties | | | |
|---|---|---|---|---|---|---|---|---|
| | (%) | E (MPa) | σ (MPa) | ε (%) | E (MPa) | σ (MPa) | ε (%) | $U_t$ (MJ m$^{-3}$) |
| Cartilage | | | | | | | | |
| Porcine Cartilage | 76.5 ± 2.12 | — | — | — | 1.04 ± 0.35 | 30.6 ± 6.5 | 77.8 ± 9.9 | 7.03 ± 2.37 |

EWC = equilibrium water content,
E = elastic modulus,
σ = stress,
ε = strain,
$U_t$ = compressive toughness (deformation energy)

Figure 4A:
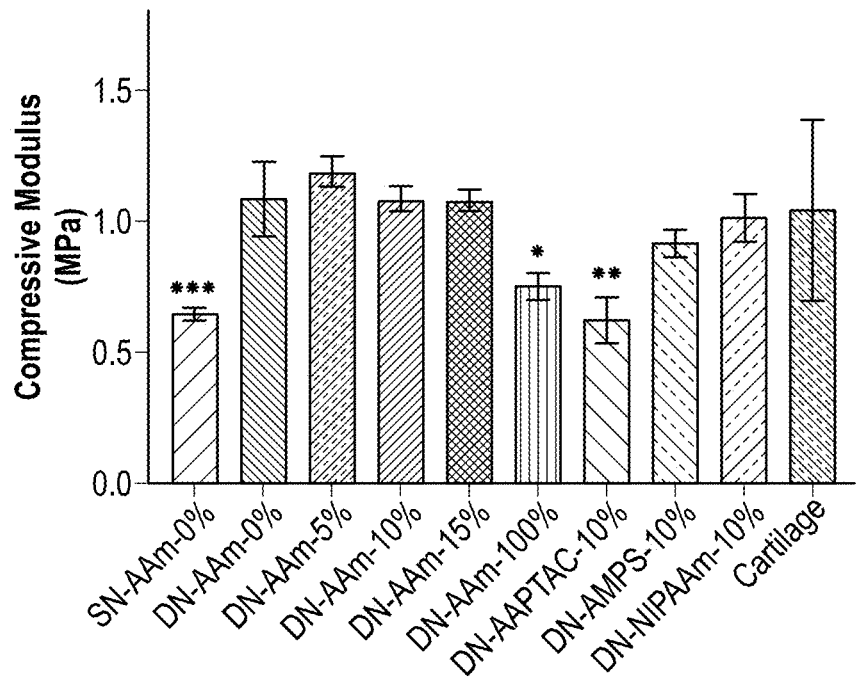
FIGS. 4A and 4B illustrate compressive modulus (FIG. 4A) and compressive strength (FIG. 4B) of additional controls compared to porcine articular cartilage. All *'s indicate statistical significance from cartilage, in which "*" represents p<0.05, "" represents p<0.01, "*" represents p<0.001 and "****" represents p<0.0001.
Figure 4B:
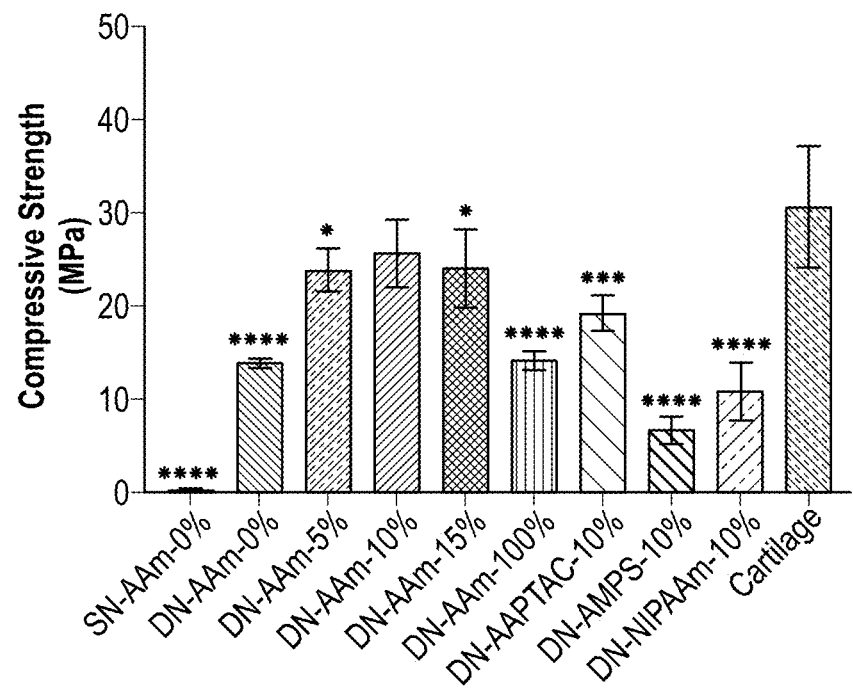

Interestingly, the addition of increasing amounts of AAm (5, 10 or 15 wt % based on NIPAAm) did not result in significant differences in tensile or compressive modulus, strength and toughness between the AAm-containing DNs (FIGS. 3A-3D, Table 2). However, the VPTT values (Table 1, FIG. 2) systematically increased with increasing levels of AAm, indicating a gradual increase in hydrophilicity and successful incorporation of AAm into the PNIPAAm network. It is hypothesized that the addition of the less-bulky AAm segments increases the overall mobility of the second network allowing for greater energy dissipation while not hindering the chain stiffening induced by the electrostatic repulsion of the anionic PAMPS first network and the physical interactions between the PNIPAAm chains of the second network. To further confirm this enhancement of strength and modulus was unique to the combination of NIPAAm and AAm, several additional controls, including the addition of anionic (AMPS, "DN-AMPS-10%") and cationic 3-(acrylamidopropyl)trimethylammonium chloride (AAPTAC, DN-AAPTAC-10%") comonomers at 10 wt % to the PNIPAAm second network as well as an AAm only (2.0 M, no NIPAAm, "DN-AAm-100%") second network were evaluated. Additionally, to eliminate concentration as a variable, an extra 10 wt % NIPAAm was added to the original 2.0 M NIPAAm second network denoted as "DN-NIPAAm-10%" which displayed similar properties to the DN-AAm-0% control. Notably, none of these controls exhibited the same combination of cartilage-like mechanical properties as the DN-AAm-10% (FIGS. 4A-4B), demonstrating the importance of using AAm, a small, non-ionic, hydrophilic comonomer, as the additive.

Figure 5A:
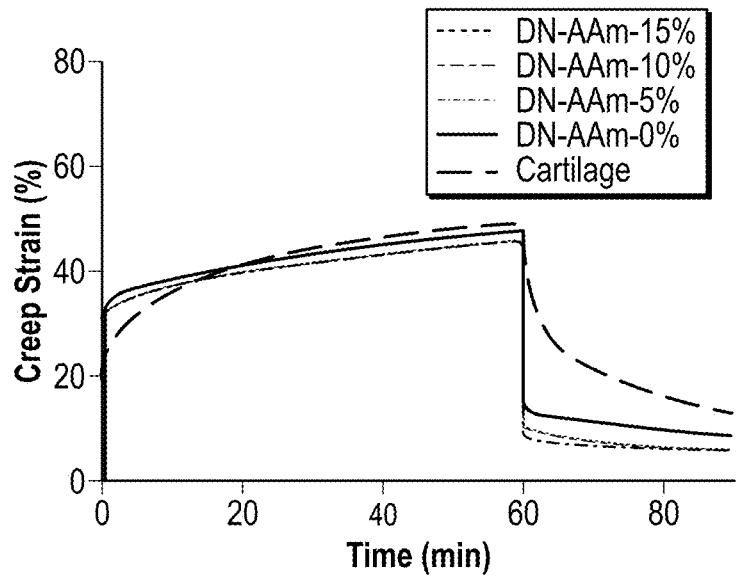
FIG. 5A shows creep response of the PAMPS/P(NIPAAm-co-AAm) DN hydrogel series comparing the viscoelastic behavior of the DNs to porcine cartilage and FIG. 5B shows the percent recovery immediately after removal of load (t=0, solid) and 30 min after removal of load (t=30, striped).
Figure 5B:
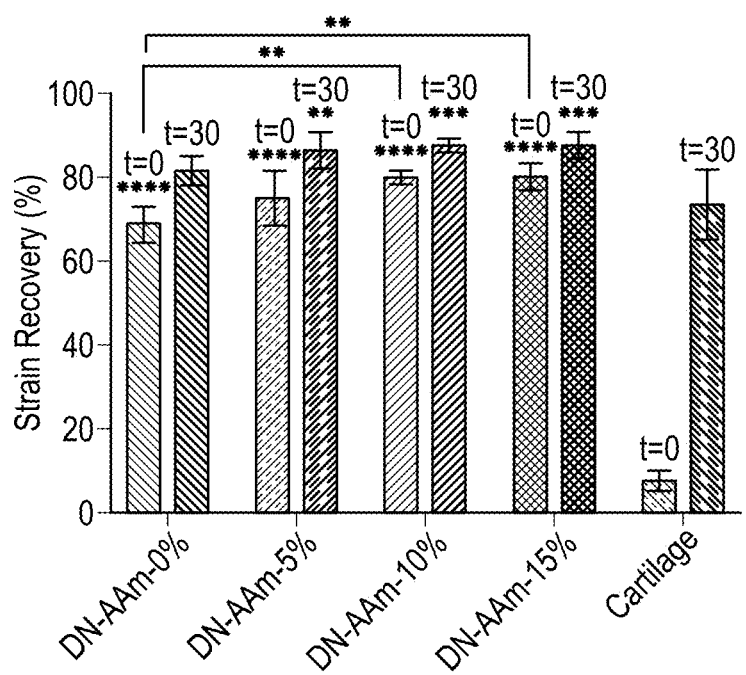

After confirming the general swelling and mechanical properties of the DN hydrogels were desirable for synthetic cartilage (Table 2), additional cartilage-specific characteristics were assessed including viscoelasticity and lubricity. To evaluate the viscoelastic properties of the DN hydrogels versus that of the cartilage, the creep response as well as subsequent recovery was observed after applying a constant stress of 0.35 MPa, representative of the normal averaged joint stress, for one hour. As seen in FIG. 5A, the initial creep strain immediately reached after step compression was slightly higher for the DN hydrogels (~35% strain) than for the cartilage (~25% strain). However, due to the larger creep deformation of the cartilage over time, both the DN hydrogels and the cartilage reached a similar final creep strain (~50%, FIG. 5A). It is hypothesized that the creep deformation of the DN hydrogels is reduced by strong electrostatic repulsive forces as well as covalent crosslinking that reduces molecular deformation and relaxation of the polymer network. While cartilage similarly consists of electrostatic proteoglycans as well as collagen, these form duplexes based on physical rather than covalent bonds, allowing for molecular movement through the breaking and reforming of these reversible interactions. Thus, cartilage will exhibit a larger amount of creep flow when exposed to the same step stress as the DN hydrogels. This ability of chemical crosslinking to enhance the long-term stability of hydrogels has been demonstrated previously. Therefore, the inherent difference in structure of covalently crosslinked hydrogels compared to biological tissue explains the more elastic response exhibited by the DN hydrogels compared to the slower, more viscous nature of cartilage. Likewise, this trend in response was also seen during recovery, in which the DN hydrogels recovered much more rapidly than cartilage. The slower recovery of cartilage can be attributed to the gradual formation of new physical interactions within the proteoglycan/collagen matrix. In contrast, the covalent crosslinks of the DN hydrogels facilitate a more elastic creep recovery. Notably, the AAm-containing DNs recovered to a greater extent than the "1.5-AMPS-0%" control without AAm (FIG. 5B). During this brief creep analysis, intended to limit dehydration, full recovery was not observed for the cartilage or hydrogel specimens.

Figure 5C:
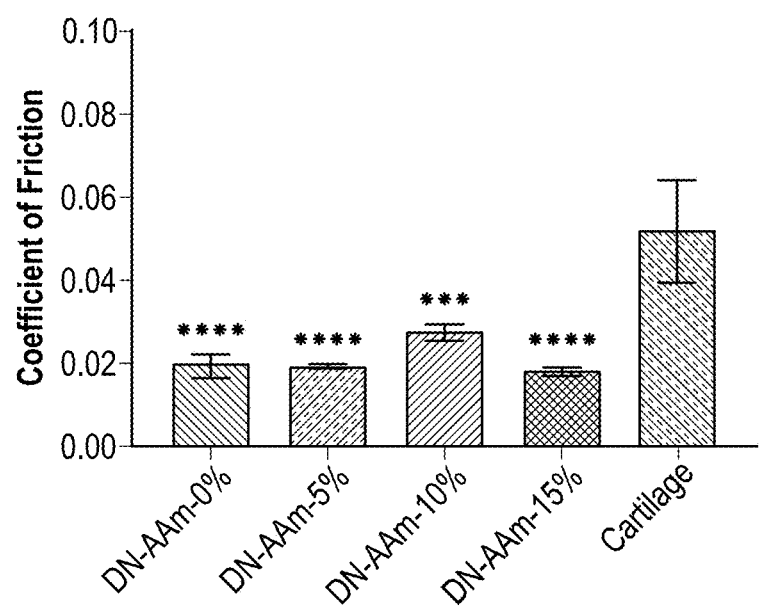
FIG. 5C shows (coefficient of friction) COF of the PAMPS/P(NIPAAm-co-AAm) DN hydrogel series comparing the lubricity of the DNs to porcine cartilage. All *'s indicate statistical significance from cartilage at respective time points unless otherwise denoted, in which "" represents p<0.01, "*" represents p<0.001 and "****" represents p<0.0001.
Figure 6C:
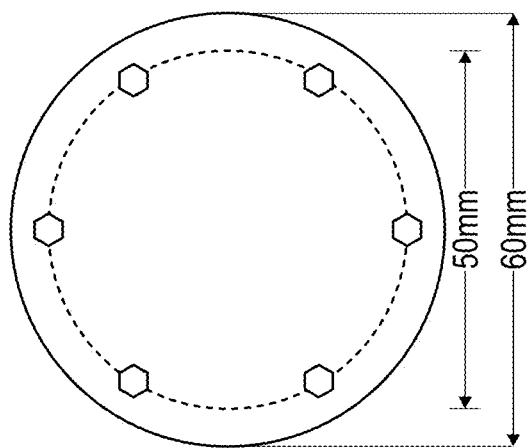
FIGS. 6A, 6B and 6C illustrate friction testing (tribology) specimen clamp for use according to aspects of the disclosure.
Figure 6B:
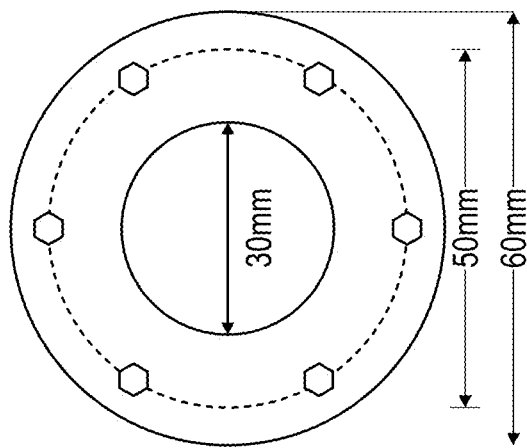
Figure 6A:
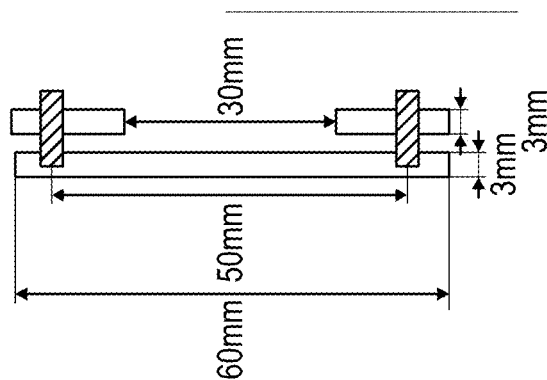
Figure 7A:
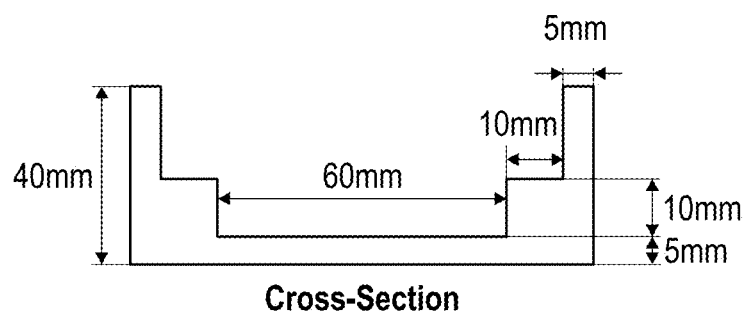
FIGS. 7A, 7B and 7C illustrates a friction testing (tribology) submersion chamber for use according to aspects of the disclosure.
Figure 7B:
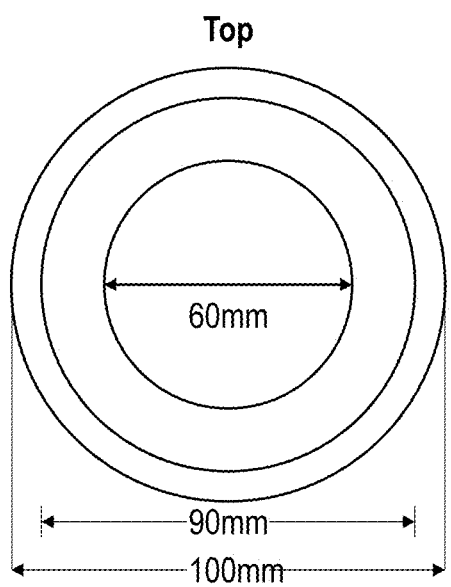
Figure 7C:
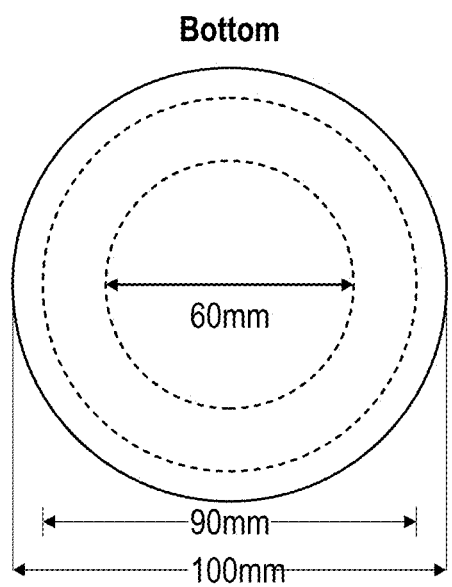

One of the purposes of cartilage is to provide an articulating surface with high lubricity. Thus, the COF of the DN hydrogels was assessed through standard pin-on-disc tribological methods. A ceramic ball bearing was chosen as the pin to represent a common biomaterial used in total knee replacements. To simulate synovial fluid present in joints, a dilute FBS solution (adopted from ASTM F732) was utilized as the lubricant with a protein concentration similar to that of healthy synovial fluid. To hold the hydrogel specimens in place in a hydrated environment, a custom clamp (FIGS. 6A-6C) and submersion chamber (FIGS. 7A-7C) were built. A constant load of 5 N was applied to achieve contact pressures of ~0.6 MPa, well within the range of normal average joint stresses. As a direct comparison to native tissue, a strip of harvested porcine cartilage was evaluated similarly. Notably, all DN hydrogel compositions exhibited significantly lower COF values versus the cartilage (FIG. 5C). Thus, these hydrogels have great potential to perform as well as healthy cartilage as a synthetic articulating surface with high lubricity.

Figure 8:
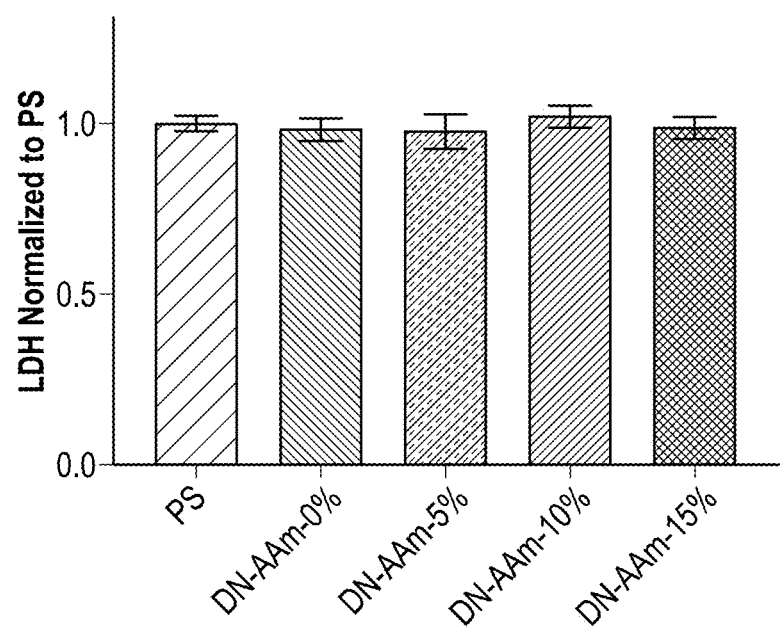
FIG. 8 shows normalized lactate dehydrogenase absorption confirming cytocompatibility of the PAMPS/P(NIPAAm-co-AAm) DN hydrogel series.
Figure 9A:
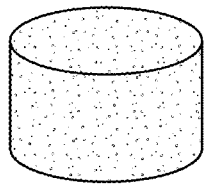
FIGS. 9A, 9B, 9C and 9D illustrate cartilage mimetic hydrogels according to various embodiments of the present disclosure.
Figure 9B:
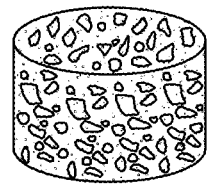
Figure 9C:
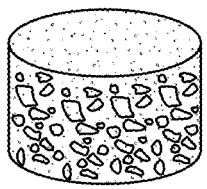
Figure 9D:
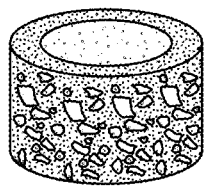
Figure 10:
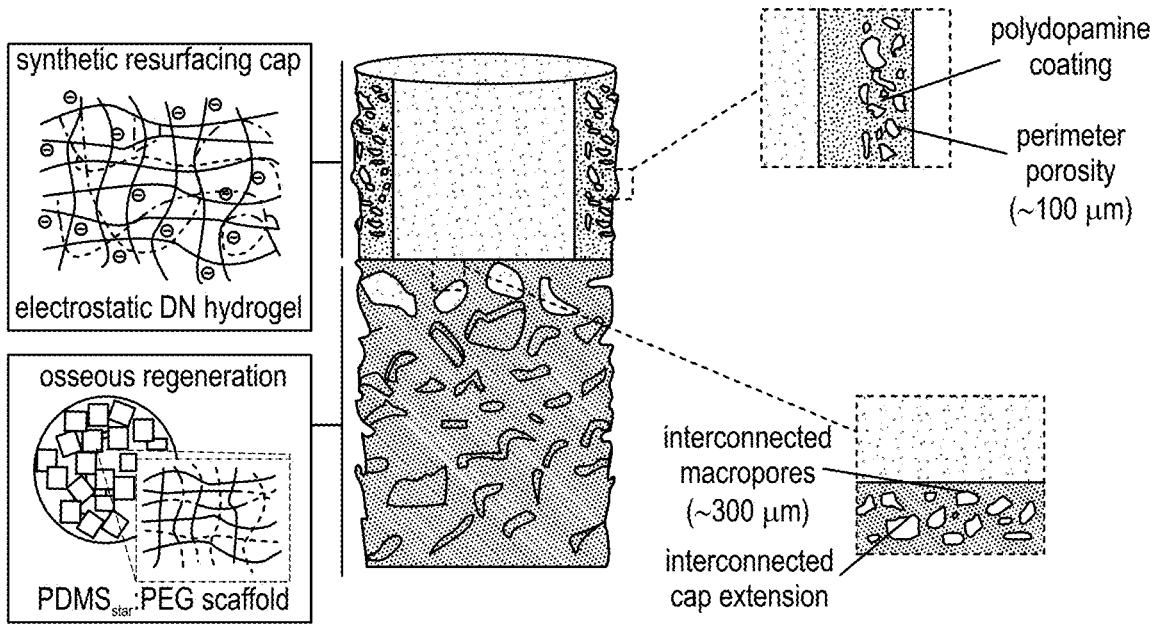
FIG. 10 illustrates combined design with porous regenerative hydrogel scaffold according to an embodiment of the present disclosure.

Lastly, to confirm cytocompatibility, mesenchymal progenitor 10T1/2 cells were seeded onto all DN hydrogel compositions and an LDH assay was performed on the surrounding media after 24 hours of incubation. Tissue culture polystyrene (PS) represented a cytocompatible control and thus, all LDH absorption was normalized to PS. LDH levels of all hydrogel specimens were determined similar to the PS control (FIG. 8), confirming cytocompatibility of the DN hydrogels. Notably, the addition of AAm into the PNIPAAm second network produced a reduction in cell adhesion as observed through brightfield microscopy, which demonstrated reduced cell adhesion with increasing AAm comonomer after 24-hour incubation of 10T1/2 cells on the surface of the PAMPS/P(NIPAAm-co-AAm) DN hydrogel series and polystyrene (PS) as an adhesive control. This trend showed a direct correlation between increased hydrophilicity and decreased cellular attachment. Although the observed results were expected due to the known higher affinity of proteins and thus cells to more hydrophobic surfaces, the prominent differences seen in cellular response with only small additions of AAm (~5-10%) demonstrated the facile tunability of these DN hydrogels.

Disclosed herein is a cartilage-mimetic hydrogel that could serve as a synthetic cartilage substitute for current cartilage defect treatment methods such as focal resurfacing and autograft transplantation (FIGS. 9A-9D and FIG. 10). Through the use of a PNIPAAm-based DN hydrogel design, the modulus, strength and toughness were enhanced simultaneously without reducing the water content, something not previously achieved in other hydrogels. Interestingly, the addition of AAm not only achieved the intended dimensional stability by tuning of the VPTT out of the physiologic range, but also significantly enhanced the compressive strength (~25 MPa) of the membranes while maintaining a cartilage-like modulus (~1 MPa) and hydration (~80%). Although the PAMPS/P(NIPAAm-co-AAm) DN hydrogels exhibited a more elastic response compared to cartilage, the final creep strain of the each were nearly equal after 1 hour indicating they may reach a similar equilibrium strain under the same constant stress. As expected based on their covalent nature, the recovery of the DN-AAm hydrogels was more rapid than the porcine cartilage, both reaching >75% recovery after 30 minutes. Most notably, all DN hydrogels reported herein achieved significantly lower COF values versus native cartilage. This ability to mimic the hydration, stiffness, strength and lubricity of cartilage as well as demonstrate resistance to creep make these PNIPAAm-based DN hydrogels promising candidates as synthetic cartilage grafts.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A cartilage mimetic gel comprising:
   double network hydrogels,
      wherein the double network hydrogels comprise a first crosslinked network formed from poly(2-acrylamido-2-methylpropane sulfonic acid) and a second crosslinked network.

2. The cartilage mimetic gel of claim 1, wherein the second crosslinked network is formed from poly(N-isopropyl acrylamide-co-acrylamide).

3. The cartilage mimetic gel of claim 1, wherein at least one of the first crosslinked network and the second crosslinked network comprises a comonomer.

4. The cartilage mimetic gel of claim 1, wherein the double network hydrogels comprise a comonomer selected from the group consisting of a zwitterionic comonomer, a hydrophilic comonomer, a neutral comonomer, an anionic comonomer, a cationic comonomer, or combinations thereof.

5. The cartilage mimetic gel of claim 1, further comprising a third crosslinked network that comprises at least one of a zwitterionic comonomer, a hydrophilic comonomer, a neutral comonomer, an anionic comonomer, a cationic comonomer, or combinations thereof.

6. The cartilage mimetic gel of claim 1, wherein the double network hydrogels are porated.

7. The cartilage mimetic gel of claim 1, wherein the double network hydrogels are coated with polydopamine.

8. The cartilage mimetic gel of claim 1, wherein the double network hydrogels combined with an anchoring base.

9. The cartilage mimetic gel of claim 8, wherein the anchoring base is at least one of a regenerative polymeric scaffold, a metal, a ceramic, and an alloy.

10. A cartilage mimetic gel comprising:
    double network hydrogels,
       wherein the double network hydrogels comprise a first crosslinked network formed from poly(N-isopropyl acrylamide-co-acrylamide) and a second crosslinked network.

11. The cartilage mimetic gel of claim 10, wherein the second crosslinked network is formed from poly(2-acrylamido-2-methylpropane sulfonic acid).

12. The cartilage mimetic gel of claim 10, wherein at least one of the first crosslinked network and the second crosslinked network comprises a comonomer.

13. The cartilage mimetic gel of claim 10, wherein the double network hydrogels comprise a comonomer selected from the group consisting of a zwitterionic comonomer, a hydrophilic comonomer, a neutral comonomer, an anionic comonomer, a cationic comonomer, or combinations thereof.

14. The cartilage mimetic gel of claim 10, further comprising a third crosslinked network that comprises at least one of a zwitterionic comonomer, a hydrophilic comonomer, a neutral comonomer, an anionic comonomer, a cationic comonomer, or combinations thereof.

15. The cartilage mimetic gel of claim 10, wherein the double network hydrogels are porated.

16. The cartilage mimetic gel of claim 10, wherein the double network hydrogels are coated with polydopamine.

17. The cartilage mimetic gel of claim 10, wherein the double network hydrogels combined with an anchoring base.

18. The cartilage mimetic gel of claim 17, wherein the anchoring base is at least one of a regenerative polymeric scaffold, a metal, a ceramic, and an alloy.

* * * * *